United States Patent
Ali (10) Patent No.: US 8,070,677 B2
(45) Date of Patent: Dec. 6, 2011

(54) METHOD AND APPARATUS FOR DISTINGUISHING BETWEEN CLINICALLY SIGNIFICANT CHANGES AND ARTIFACTS IN PATIENT PHYSIOLOGICAL INFORMATION

(75) Inventor: Walid S. I. Ali, Chandler, AZ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 892 days.

(21) Appl. No.: 11/916,767

(22) PCT Filed: May 31, 2006

(86) PCT No.: PCT/IB2006/051743
§ 371 (c)(1),
(2), (4) Date: Dec. 6, 2007

(87) PCT Pub. No.: WO2006/131850
PCT Pub. Date: Dec. 14, 2006

(65) Prior Publication Data
US 2008/0208012 A1    Aug. 28, 2008

Related U.S. Application Data

(60) Provisional application No. 60/688,888, filed on Jun. 9, 2005.

(51) Int. Cl.
*A61B 5/00* (2006.01)

(52) U.S. Cl. ............... 600/301; 705/2; 702/190; 702/1

(58) Field of Classification Search .......... 600/300–301, 600/544–547, 372–385, 481, 429, 336; 128/920, 128/900–902, 921–925; 700/2
See application file for complete search history.

(56) References Cited

U.S. PATENT DOCUMENTS

| 3,636,941 | A | * | 1/1972 | Guevrekian | 600/496 |
| 4,852,570 | A | | 8/1989 | Levine | |
| 5,438,983 | A | | 8/1995 | Falcone | |
| 5,464,012 | A | * | 11/1995 | Falcone | 600/301 |
| 6,002,952 | A | * | 12/1999 | Diab et al. | 600/310 |
| 6,036,653 | A | * | 3/2000 | Baba et al. | 600/500 |
| 6,105,015 | A | * | 8/2000 | Nguyen et al. | 706/26 |
| 6,287,328 | B1 | * | 9/2001 | Snyder et al. | 600/509 |
| 6,579,232 | B2 | | 6/2003 | Sakamaki et al. | |

(Continued)

OTHER PUBLICATIONS

Saeed, M. Mark, R.G. "Multiparameter trend monitoring and intelligent displays using wavelet analysis", Computers in Cardiology 2000; 27:797-800.*

(Continued)

*Primary Examiner* — Henry M Johnson, III
*Assistant Examiner* — Marie Archer (57) ABSTRACT

A patient physiological information monitoring system includes a plurality of patient monitoring devices (6) and a physiological information analyzer (2). The plurality of patient monitoring devices (6) monitor physiological information from a patient and generate corresponding physiological signals. The physiological information analyzer (2) processes the monitored physiological information and determines whether a physiological change is a clinically significant event or an artifact. The physiological information analyzer includes at least one receiver (4) that receives the physiological signals from the patient monitoring devices; a signal correlator (10) that generates morphograms from pairs of the received physiological signals; a signature generator (12) that applies a wavelet decomposition to each morphogram to compute a signature for each morphogram; and a decision component (14) that compares the morphogram signatures within and across sampling intervals and determines if a physiological change is a clinically significant change or an artifact.

20 Claims, 5 Drawing Sheets

U.S. PATENT DOCUMENTS

2003/0097046 A1* 5/2003 Sakamaki et al. ............ 600/300
2004/0024532 A1 2/2004 Kincaid

OTHER PUBLICATIONS

Celler, B.G., et al, "Low computational cost classifiers for ECG diagnosis using neural networks", Proceedings of the 20th Annual Intl. Conference of the IEEE Engineering in Medicine and Biology society, vol. 20, No. 12, 1998, p. 1337-1340.*

Gamero, L. G. et al., "Wavelet transform analysis of heart rate variability during myocardial ischaemia", Medical & Biological Engineering & Computing, vol. 40, 2002, p. 72-78.*

Shyu, L-Y, et al., "Using wavelet transform and fuzzy neural network for VPC detection from the Holter ECG", IEEE Transactions on Biomedical Engineering, vol. 51, No. 7, Jul. 2004, p. 1269-1273.*

Mora, F. A. et al "Intelligent Patient Monitoring and Management Systems: A Review", IEEE Engineering in Medicine and Biology, Dec. 1993, p. 23-33.*

Hoyhtya A. K., "Intelligent Patient Monitoring: Detecting and Defining Significant Clinical Events", submitted to the Department of Electrical Engineering and Computer Science in partial fulfillment of the requirements for the degree of Master of Science in Electrical Engineering at the Massachusetts Institute of Technology, Jun. 1996, p. 1-84.*

Addison, P. S., et al.; A novel time-frequency-based 3D Lissajous figure method and its application to the determination of oxygen saturation from the photoplethysmogram; 2004; Meas. Sci. Technol.; 15:L15-L18.

Ali, W., et al.; Morphograms: Exploiting Correlation Patterns to Efficiently Identify Clinically Significant Events in Intensive Care Units; 2004; IEEE-EMBS; pp. 554-557.

Daubechies, I.; Ten Lectures on Wavelets; 1992; Chapter 6; pp. 194-202, 254-257, 313-319.

Heldt, T., et al.; Integrating Data, Models, and Reasoning in Critical Care; 2006; IEEE Proc. EMBS; pp. 350-353.

Mallat, S.; A Wavelet Tour of Signal Processing; 1998; Academic Press; pp. 250-252.

Pereda, E., et al.; Nonlinear multivariate analysis of neurophysiological signals; 2005; Progress in Neurobiology; 77:1-37.

Ryoo, H. C., et al.; Two compartment fusion system designed for physiological state monitoring; 2001; IEEE Proc. EMBS; pp. 2224-2227.

Saeed, M., et al.; Multiparameter Trend Monitoring and Intelligent Displays Using Wavelet Analysis; 2000; Computers in Cardiology; 27:797-800.

Ali, et al. "Morphograms: Exploiting Correlation Patterns to Efficiently Identify Clinically Significant Events in Intensive Care Units", Proceedings of 26th Annual International Conference of the IEEE EMBS, San Francisco, CA US, Sep. 1-5, 2004 pp. 554-557.

Moody, et al "A Database to Support Development and Evaluation of Intelligent Intensive Care Monitoring", Computers in Cardiology, 1996; 0276-06547/96 © 1996 IEEE.

Saeed, et al. "Multiparameter Trend Monitoring and Intelligent Displays Using Wavelet Analysis", Computers in Cardiology, 2000: 27:979-800; 0276-06547/00 © 2000 IEEE.

Ali, et al. "Identifying Artifacts in Arterial Blood Pressure Using Morphogram Variability", Session S93.1; file://D:\search_ids\RN7\searchreport\docsused\cinc.htm Mar. 4, 2005.

Ali, et al. "Identifying Artifacts in Arterial Blood Pressure Using Morphogram Variability", 4 pgs.

* cited by examiner

METHOD AND APPARATUS FOR DISTINGUISHING BETWEEN CLINICALLY SIGNIFICANT CHANGES AND ARTIFACTS IN PATIENT PHYSIOLOGICAL INFORMATION

CROSS REFERENCE TO RELATED APPLICATIONS

This application claims the benefit of U.S. provisional application Ser. No. 60/688,888 filed Jun. 9, 2005, which is incorporated herein by reference.

The following relates to patient monitoring. It finds particular application to determining whether physiological changes captured by patient monitoring devices are clinically significant or artifacts.

Many intensive/critical care unit (ICU/CCU) patients have changing physiological conditions. Such patients are prone to deterioration and may periodically need immediate intervention when a clinically significant physiological change occurs. Thus, overall treatment is improved by close and accurate monitoring of physiological changes. Such monitoring is achieved through various patient monitoring devices. Of particular importance are physiological changes that invoke patient monitoring device alarms. When valid alarms are triggered, hospital staff (e.g., doctors, nurses . . . ) begin evaluating and treating the patient. Many times, the evaluation results in concluding that the physiological change is not representative of a clinically significant change (e.g., a false alarm) or that no physiological change actually occurred (e.g., an artifact). Such alarms hinder clinical practice, obscure tru critical events, and increase the amount of human intervention in intensive/critical care situations.

To mitigate attending to every false alarm, hospital staff learn to decipher between clearly erroneous alarms (e.g., by looking at the signal or value invoking the alarm) and alarms that potentially could be associated with a clinically significant physiological change. Thus, it is not uncommon for staff to ignore a sounding alarm. However, the staff is not always able to ascertain when a sounding false alarm obscures a later occurring critical event.

In one aspect, morphograms of physiological signals acquired by patient monitoring devices are decomposed via wavelet decomposition to generate unique signatures that are compared with each other to determine whether a physiological change is associated with a change in all related signatures (a clinically significant change) or whether the physiological change is only associated with a subset of signatures with a common signal (artifact).

In another aspect, a patient physiological information monitoring system includes a plurality of patient monitoring devices and a physiological information analyzer. The plurality of patient monitoring devices monitor physiological information from a patient and generate corresponding physiological signals. The physiological information analyzer processes the monitored physiological information and determines whether a physiological change is a clinically significant event or an artifact. The physiological information analyzer includes at least one receiver that receives the physiological signals from the patient monitoring devices; a signal correlator that generates morphograms from pairs of the received physiological signals; a signature generator that applies a wavelet decomposition to each morphogram to compute a signature for each morphogram; and a decision component that compares the morphogram signatures within and across sampling intervals and determines if a physiological change is a clinically significant change or an artifact.

One advantage includes determining whether a physiological change captured with a patient monitoring device is a clinically significant change or an artifact.

Another advantage resides in mitigating patient monitoring device false alarms.

Another advantage resides in reducing monitoring cost relative to other approaches that achieve a similar accuracy.

Another advantage lies in increased patient monitoring resolution.

Still further advantages will become apparent to those of ordinary skill in the art upon reading and understanding the detailed description of the preferred embodiments.

Figure 1:
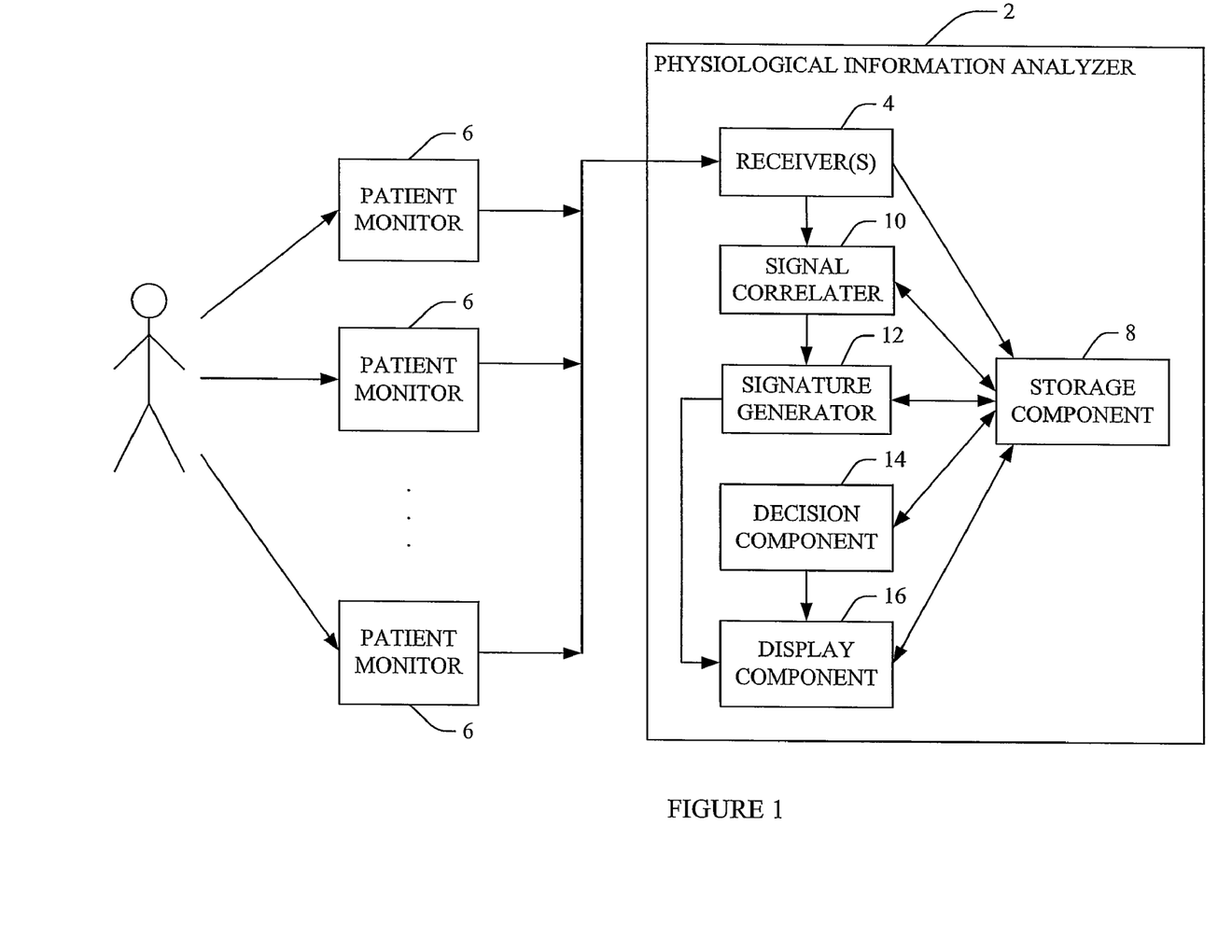
FIG. 1 illustrates a system that facilitates distinguishing between clinically significant changes and artifact in patient physiological information.

FIG. 1 illustrates a patient physiological information monitoring system for alerting clinical staff when a physiological change captured by a patient monitoring device is a clinically significant change. The patient physiological information monitoring system includes a physiological information analyzer ("analyzer") 2 that analyzes monitored patient physiological information and renders a decision whether any particular perturbation in the physiological information is associated with a clinically significant physiological change.

The analyzer 2 includes one or more receivers 4 that receive patient physiological information indicative of a physiological state of a patient. Such physiological information is obtained from one or more patient monitoring devices 6 (e.g., a cardiac monitor, a hemodynamic monitor . . . ) and/or directly from sensors (not shown) located on or proximate to the patient. By way of example, a patient with chest pain typically is monitored at a health care facility with an electrocardiograph (ECG) device that collects heart-related electrical signals from multiple ECG leads (e.g., 3 leads, 5 leads . . .) strategically positioned on the patient's body. The collected signals are processed and visually displayed (e.g., on paper or a monitor) for observance by a doctor or other medical staff. Such signals can be provided by the ECG device to one or more of the receivers 4 (e.g., through a wireless and/or wired connection). Using normally captured and processed physiological information (e.g., ECG signals) from the patient monitoring devices 6 enables seamless incorporation of the analyzer 2 into existing patient monitoring equipment without any need for software, hardware, or architectural changes to the patient monitoring equipment. Other monitoring devices monitor other physiological data, such as blood pressure, blood oxygen, respiration, and the like, and communicate the physiological data from the monitor to the receivers 4.

Each of the receivers 4 is independently configured to collect physiological information from one or more of the patient monitoring devices 6. A receiver configured to collect physiological information from more than one of the patient monitoring devices 6 can collect such information concurrently through parallel channels or serially through a shared or one or more dedicated channel. Where more then one of the receivers 4 collects physiological information from more than one of the patient monitoring devices 6, a subset of the receivers 4 may collect physiological information from the same monitoring device or a similar group of monitoring devices.

Each of the receivers 4 periodically collects physiological information during a sampling interval at a sampling rate (e.g. collect data for X seconds every Y seconds, where X and Y are positive real numbers and $X \leq Y$). The sampling interval and rate for any one receiver is based at least in part an alarm configuration of the patient monitoring device that is monitoring the physiological information, resolution, processing power and memory size of the analyzer 2, and the discretion of the attending clinician. For instance, with a typical patient monitoring device, physiological conditions in the alarm range are monitored over a period of time (latency period) before a related alarm occurs in order to reach stability (e.g., and trigger an alarm with a high degree of correctness) and mitigate false alarms due to patient movement, erroneous signals, etc. For example, a series of anomalous blood pressure readings may be monitored for about a twelve second (e.g., the actual time is patient monitoring device/manufacturer dependent) period of analysis preceding invocation of a blood pressure alarm. If the blood pressure readings move out of the alarm range prior to lapse of the latency period, the blood pressure alarm is not triggered; but, if the blood pressure readings remain within the alarm condition range, the blood pressure alarm triggers upon lapse of the latency period.

The sampling rate of a particular receiver is a fraction of the latency period of the associated monitoring device so that the analyzer 2 may render a decision as to whether a significant physiological change has occurred prior to or when a patient monitoring device sounds an alarm. In another embodiment, the analyzer 2 sounds an alarm (e.g., its own alarm displays at a central monitoring station or it invokes a monitoring device to prematurely alarm) when it determines a clinically significant physiological change has occurred. Such alarm condition may be determined by the analyzer 2 well before the monitoring device latency period lapses, thereby reducing the time between a clinically significant physiological change and treatment thereof. In still another embodiment, the analyzer 2 can send a signal to the patient monitoring device to prevent or turn off an alarm when the analyzer 2 determines a physiological change is an artifact.

In the illustrated embodiment, the receivers 4 convey the physiological information to a signal correlater 10 for further processing or for storing the received physiological information in a storage medium 8 (e.g., RAM, cache . . . ). The physiological information is conveyed/stored such that the data is separable based at least in part on monitoring device and sampling interval and time. Thus, physiological information associated with a particular monitoring device and/or collected during a particular sampling interval can be identified and retrieved. For example, physiological information from an ECG that was collected during a kth (where k is an integer greater than one) sampling interval can be identified from within all the physiological information collected over all the sampling intervals.

More specifically, the signal correlater 10 generates a morphogram for pairs of signals with physiological information captured during contemporaneious sampling intervals. Thus, if the physiological information includes information from N different monitoring devices, then the theoretical maximum number of morphograms generated for that sampling interval is $$\sum_{1}^{N-1} X,$$

where X is the variable summed over. If data is collected for L (where L is an integer greater than one) sampling intervals, then the theoretical maximum number of morphograms at any given time is $$L \sum_{1}^{N-1} X.$$

The actual number of morphograms generated and/or saved depends on factors such as a resolution and processing power, the size of storage medium 8, and the monitoring clinician. The generated morphograms are conveyed to a signature generator 12 for further processing, displaying, or storage in the storage medium 8.

Figure 2:
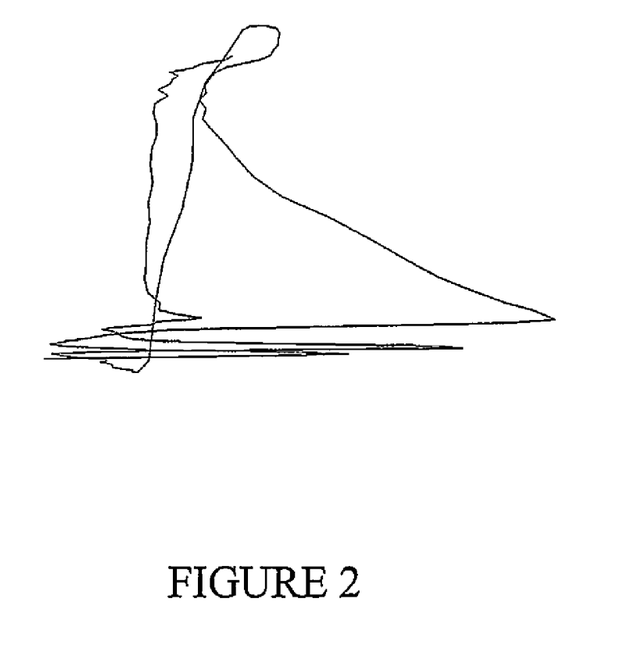
FIG. 2 illustrates an exemplary ECG-ABP morphogram.

Each morphogram is a mapping of one physiological signal against another. It illustrates how the two physiological signals move together. The ability of one type of physiological signal to follow another type of physiological signal depends on the correlation between the two types of physiological signals. In the patient monitoring domain, the morphogram depicts a relationship between physiological data such as an ECG signal and an arterial blood pressure (ABP) signal. This relationship can be mapped and visually presented using tools such as plot or graphs. For instance, the ECG data can be mapped to one axis and the ABP data can be mapped to another axis, such that the relationship is visually depicted through multi-dimensional graph. FIG. 2 illustrates an ECG-ABP morphogram in which an ECG signal is mapped to a vertical axis and an ABP signal is mapped to a horizontal axis. This mapping between physiological signals can also be represented symbolically through an equation.

The signature generator 12 computes a signature for each morphogram in each of the sampling intervals and stores the signatures in the storage medium 8. The signatures are stored based on patient monitoring device and sampling interval. For example, a signature for an ECG-ABP morphogram generated using ECG and ABP signals from an ith (where i is an integer greater than one) sampling interval can be identified from the other signatures. Because all physiological conditions do not have the same cycle periodicity, some morphograms may be based on different sampling intervals. The number of signatures stored at any given time is based at least in part on a size of the storage medium 8, the computation power of the analyzer 2, and the clinician monitoring the patient, for example.

Figure 3:
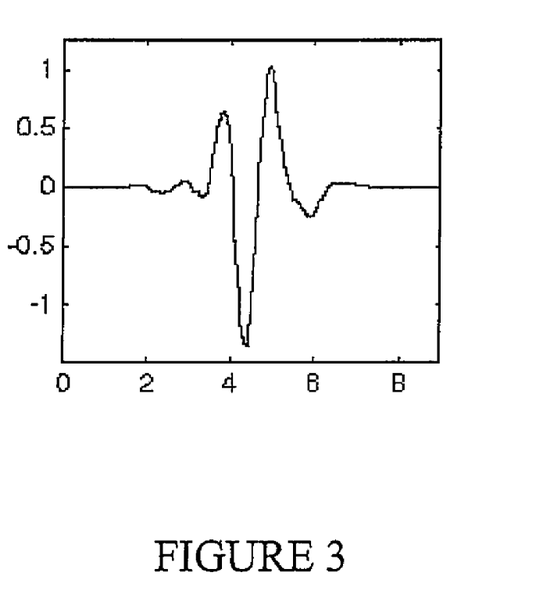
FIG. 3 illustrates an exemplary Symlet wavelet.

The signature of each morphogram is a unique shape descriptor that represents morphogram shape characteristics such as inflection points, curvature, etc. Suitable transforms for generating shape descriptors include wavelet transforms and the like. In a preferred embodiment, the morphograms are processed with a two-dimensional (2D) wavelet transform (2D wavelet decomposition). FIG. 3 illustrates a Symlet wavelet, which is the preferable 2D wavelet to use with ECG and ABP based morphograms since they have similar shape characteristics. Of course, 3D wavelet transforms can be used where three signals are correlated, and so on for higher orders.

Two-dimensional wavelet decomposition of a morphogram renders a set of coefficients that describe each morphogram in a horizontal, a vertical, and a diagonal (which includes both horizontal and vertical components) detail. With highly correlated physiological signals, a set of three coefficients fully characterizes the 2D morphogram. More levels of detail can be employed, if desired or needed, to generate more coefficients and, potentially, more accurate analysis at the cost of computational resources. Typically, more levels of decomposition facilitate capturing shape variability for morphograms generated from less correlated signals. For instance, characterizing a sine wave with a square wavelet (low degree of correlation) generally requires more levels of decomposition than characterizing the sine wave with a sinc wavelet (higher degree of correlation).

A decision component 14 compares signatures (coefficients) within and across a set of sampling intervals. Such comparison detects perturbations in related signatures, which are indicative of physiological changes. For example, a physiological change in the heart can result in changes to either or both of ECG and ABP signals which result in changes to the morphograms and signatures generated therefrom. Upon using a signature to determine whether a physiological change is a clinically significant event or an artifact, the signature can be retained (e.g., for further use or as a historical record) or discarded (e.g., deleted, written over . . . ).

Figure 4:
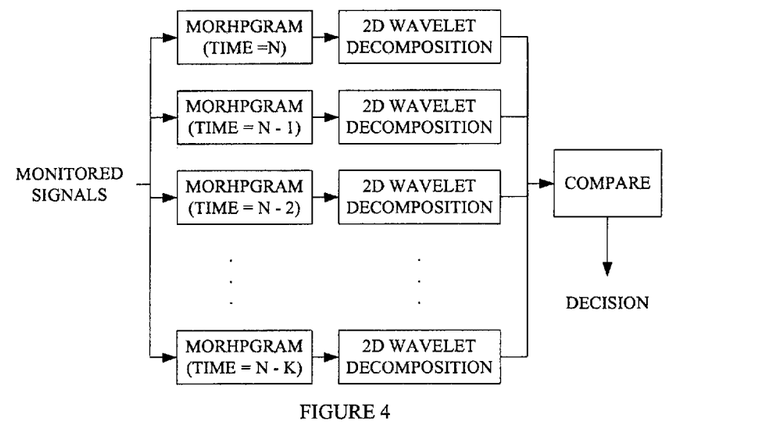
FIG. 4 illustrates a routine for signature comparison over N-K sampling intervals.

The comparison is also used to determine whether a detected physiological change is a clinically significant physiological changes or artifact. It is to be appreciated that a change in the signature can be clinically significant even if neither monitor condition changes beyond its alarm threshold. In this way, clinically significant events may be detected early. The decision component 14 determines whether a physiological change is a clinically significant change based on the shape perturbation in the signatures and signals related to the physiological change. The decision component 14 determines that a physiological change is an artifact if the shape perturbation is in a subset of signatures with at least one common signal. FIG. 4 shows an example in which signatures of morphograms generated over N-K sampling intervals are compared to render a decision.

Figure 5:
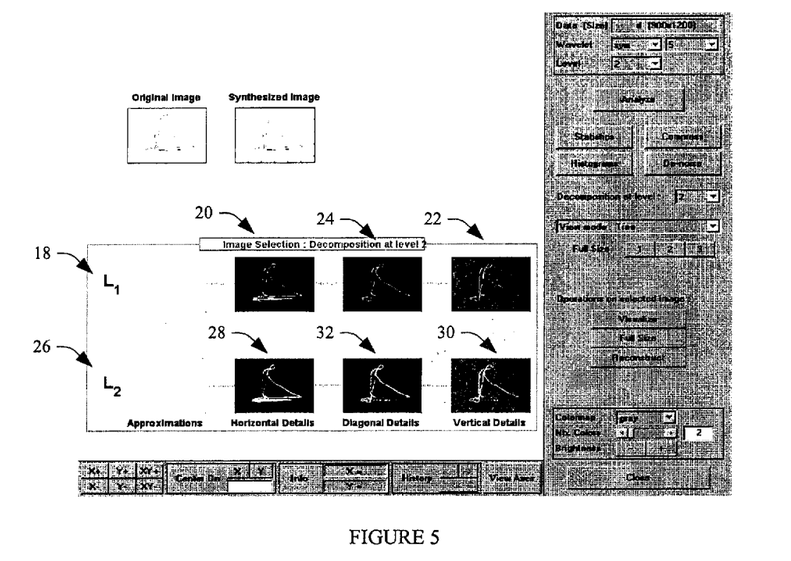
FIG. 5 illustrates an exemplary graphical user interface for displaying signature coefficients.

A display component 16 visualizes the signatures for observance by the clinical staff. Such display can be at the bedside of the patient and/or at a remote monitoring station (e.g., a nurse station, over the Internet . . . ). FIG. 5 illustrates an exemplary graphical user interface displaying coefficients for a two level, 2D Symlet wavelet decomposition of the ECG-ABP morphogram depicted in FIG. 2. A first level of decomposition (L1) 18 includes a horizontal detail 20, a vertical detail 22, and a diagonal detail 24, and a second level of decomposition (L2) 26 includes a horizontal detail 28, a vertical detail 30, and a diagonal detail 32.

Figure 6:
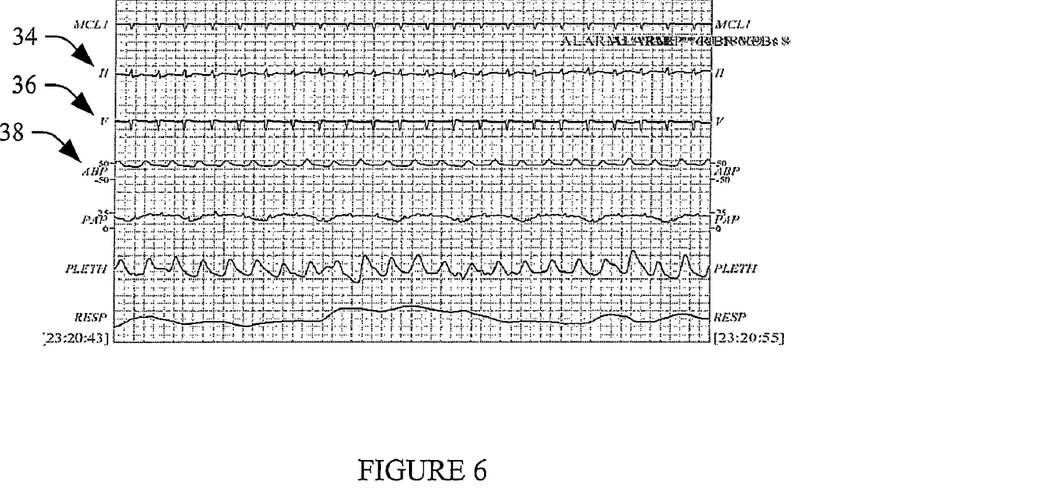
FIG. 6 shows several plots of a typical set of physiological signals captured over time for a patient with respiratory failure.

FIGS. 6-15 provide a particular example in which the analyzer 2 receives at least an ABP and two ECG signals from the patient monitoring devices 6. FIG. 6 shows several plots of a typical set of physiological signals captured over time for a patient with respiratory failure. The set of signals includes an ECG lead II signal 34, an ECG lead V signal 36, and an ABP signal 38.

Figure 7:
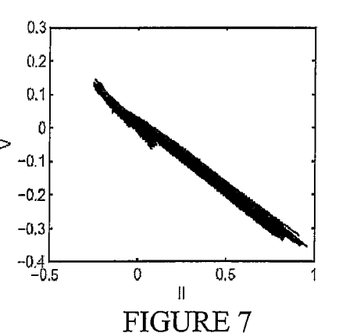
FIGS. 7-9 illustrate three example morphograms generated from pairs from an ABP and two ECG signals.
Figure 8:
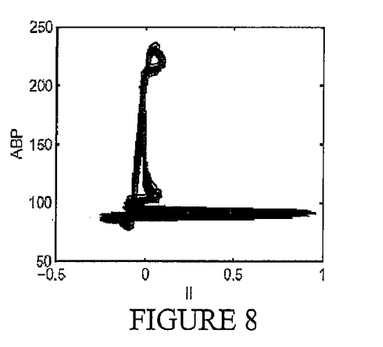
Figure 9:
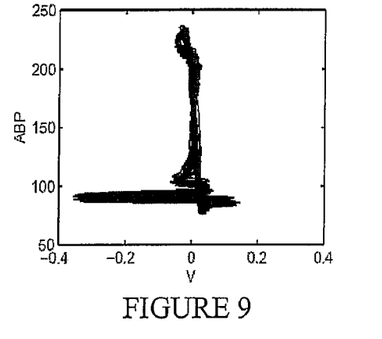

The signal correlater 10 generates morphograms for at least the ECG lead II signal 30, the ECG lead V signal 36, and the ABP signal 38. Examples of three morphograms generated from pairs of the signals 34-38 without changes or artifact are depicted in FIGS. 7-9. In particular, FIG. 7 illustrates a morphogram generated from the ECG signal II/ECG signal V pair; FIG. 8 illustrates a morphogram generated from the ECG signal II/ABP signal pair; and FIG. 9 shows a morphogram generated from the ECG signal V/ABP signal pair.

The morphograms in FIGS. 7-9 all have well-defined shapes that repeat with each as long as there are no artifacts and the patient is not undergoing physiological changes. Since ABP and the various ECG signals are highly correlated, the resulting morphogram represent characteristic morphology that represent the correlated signals for a single heart beat when the sampling rate is greater than one heart beat. In many instances, the ECG-ECG and ABP-ECG morphograms have characteristic shapes that can be generalized across patients.

Since the ABP wave lags behind the QRS complex, the ABP-ECG morphograms in FIGS. 8 and 9 have a characteristic "L" shape (or a backwards "L" shape). When the ABP is at a low value, the ECG approaches its maximum (or minimum). Similarly, when the ECG approaches a neutral value, the ABP approaches a maximum. This correlation between ABP and ECG signals accounts for the characteristic "L" shape. The pattern of the ECG-ECG morphogram in FIG. 7 lies along a diagonal typically about 45 degrees or 135 degrees (e.g., as a bar or an oval). This shape results since both signals reach extremes (e.g., some point in the QRS complex) in unison.

Figure 10:
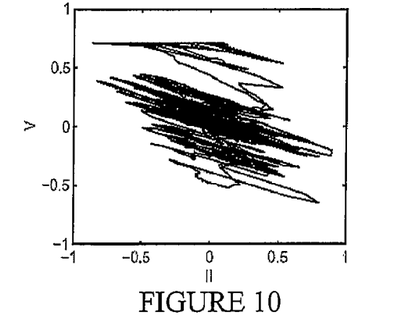
FIGS. 10-12 show graphical examples of morphograms perturbed due to physiological changes in a patient's condition.
Figure 11:
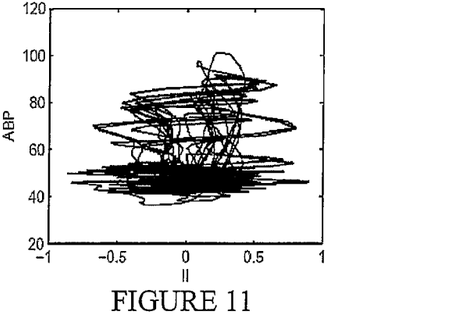
Figure 12:
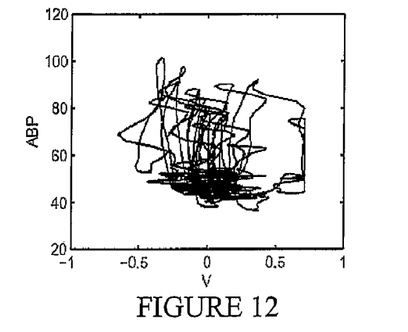
Figure 13:
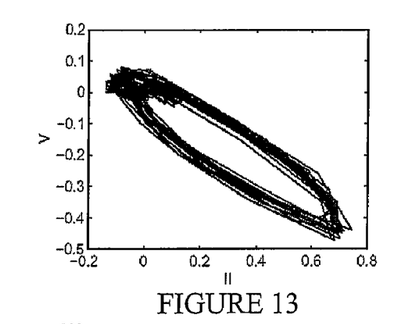
FIGS. 13-15 show graphical examples of morphograms perturbed due to an artifact.
Figure 14:
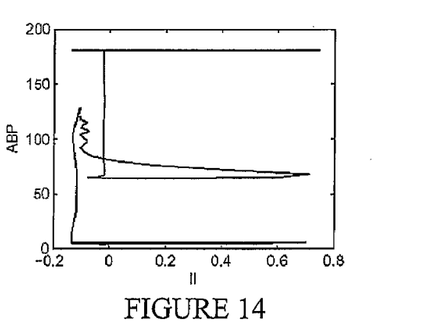
Figure 15:
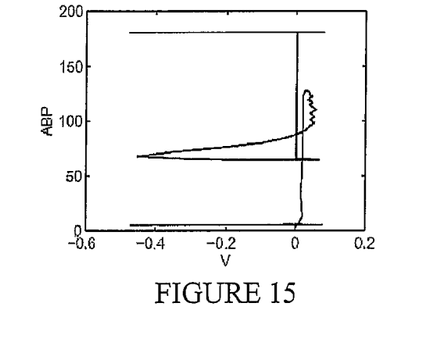

Morphograms showing significant departures from the signature are easily detected. Similarly, a morphogram that is changing over time (e.g., a gradual shorting along one leg of the "L") can be detected, and its rate of change can be clinically significant. These departures indicate either a physiologically change or an artifact. The underlying heuristic is that physiologically change is more likely to affect all signals, and thus there will be perturbations in all morphograms, whereas artifacts are more likely to affect only a single signal, and thus there will be perturbations only in the morphograms involving that signal. FIGS. 10-12 show graphical examples where the morphograms are perturbed due to physiological changes in the patient's condition. The changes in the patterns (relative to the patterns with no physiological changes or artifact shown in FIGS. 7-9) are obvious in the morphograms generated from that signal; there are perturbations in each of the morphograms' morphology. FIGS. 13-15 shows a graphical example for a patient with pulmonary edema during a time period in which an artifact occurs in the ABP signal. As depicted, only the morphograms that include the ABP signal (FIGS. 14 and 15, are perturbed; the morphogram in FIG. 13 for the two ECG signals retains its characteristic diagonal-oval shape; whereas, the two morphograms in FIGS. 14 and 15 with the ABP signal and either of the two ECG signals are highly distorted. Given that the signals in this example are highly correlated, the change in only the morphograms in FIGS. 14 and 15 indicate an artifact (e.g., a mechanical problem for that signal).

The signature generator 12 computes a signature or unique shape descriptor that characterizes the ECG-ECG and two ECG-ABP morphograms. As noted previously, in the preferred embodiment (and in this example) a 2D Symlet wavelet is used to generate morphogram signatures. The decision component 14 compares signatures (coefficients) within and across a predefined number of sampling intervals. Such comparison is used to detect physiological changes and determine whether they are clinically significant physiological changes or artifact. The decision component 14 determines a physiological change is a clinically significant change if the shape perturbation is in the signatures generated from signals related to the physiological change. Similarly, the decision component 14 determines a physiological change is an artifact if the shape perturbation is only in a subset of signatures with at least one common signal and signatures of related signals from different monitors are not. One or more of the signatures are displayed in an interface for monitoring by the medical staff.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A patient physiological information monitoring system, comprising:
   a plurality of patient monitoring devices that monitor physiological information from a patient and generate corresponding physiological signals; and
   a physiological information analyzer including one or more processors that processes the monitored physiological information and determines whether a physiological change is a clinically significant event or an artifact, the one or more processors being programmed to:
   receive the physiological signals from the patient monitoring devices;
   generate morphograms of one physiological signal versus another physiological signal from pairs of the received physiological signals within sampling intervals;
   apply a wavelet decomposition to each morphogram to compute a signature for each mapping morphogram;
   compare the morphogram signatures within and across the sampling intervals for a shape perturbation; and
   determine whether the shape perturbation is a result of a clinically significant change or an artifact.

2. The patient physiological information monitoring system as set forth in claim 1, wherein the one or more processors are further programmed to:
   determine that the physiological change is an artifact in response to the shape perturbation being only in a subset of the signatures with at least one common signal.

3. The patient physiological information monitoring system as set forth in claim 1, wherein the one or more processors are further programmed to:
   determine that an alarm is valid in response to the shape perturbation which indicates a physiological change.

4. The patient physiological information monitoring system as set forth in claim 1, further including:
   a display component that visually presents at least some of the signatures for observation by a clinical staff.

5. The patient physiological information monitoring system as set forth in claim 1, wherein the one or more processors are further programmed to:
   discard signatures that include an artifact and stores signatures that include clinically significant physiological changes in a storage component.

6. The patient physiological information monitoring system as set forth in claim 1, wherein the wavelet is a Symlet wavelet.

7. The patient physiological information monitoring system as set forth in claim 1, wherein the signature of each morphogram is represented by one or more coefficients that fully describe a shape variability of the morphogram.

8. The patient physiological information monitoring system as set forth in claim 7, wherein the one or more coefficients describe a horizontal component, a vertical component, and a diagonal component.

9. The patient physiological information monitoring system as set forth in claim 1, wherein the wavelet decomposition includes a plurality of levels of decomposition.

10. A patient physiological information monitoring system comprising:
    a plurality of patient monitoring devices that monitor physiological information from a patient and generate corresponding physiological signals; and
    a physiological information analyzer including one or more processors that processes the monitored physiological information and determines whether a physiological change is a clinically significant event or an artifact, the one or more processor being programmed to:
    receive the physiological signals sampled by the patient monitoring devices during successive sampling intervals;
    generate morphograms from pairs of the received physiological signals in each of the sampling intervals;
    compute a signature for each morphogram; and
    compare the morphogram signatures of a current and prior sampling intervals for a shape perturbation to determine if a physiological change is a clinically significant change or an artifact,
    wherein the sampling intervals occur at a sampling rate that is less than or equal to an alarm latency period of the corresponding patient monitor device, the alarm latency period corresponding to a time over which an alarm condition persists in order to trigger an alarm with a high degree of correctness.

11. The patient physiological information monitoring system as set forth in claim 10, wherein the monitored physiological information includes at least one or more electrocardiogram (ECG) signals and an arterial blood pressure (ABP) signal.

12. The patient physiological information monitoring system as set forth in claim 10, wherein the physiological information analyzer sounds an alarm and/or prematurely invokes a monitoring device to alarm when it determines a clinically significant physiological change has occurred.

13. The patient physiological information monitoring system as set forth in claim 10, wherein the physiological information analyzer prevents or turns off a patient monitoring device alarm when the analyzer determines a monitored physiological change is an artifact.

14. A method for determining whether a physiological change captured by a patient monitoring device is a clinically significant change or an artifact, comprising:
    receiving physiological signals captured by a patient monitoring device indicative of physiological information monitored from a patient;
    with one or more processors, generating a mapping of one physiological signal versus another physiological signal for pairs of the physiological signals as the physiological information for each sampling interval is received;
    with the one or more processors, applying a wavelet decomposition on each mapping to generate a signature for each mapping;
    with the one or more processors, comparing the mapping signatures within and across sampling intervals for signature perturbations;
    with the one or more processors, determining whether the signature perturbations are a result of a clinically significant change or an artifact; and with the one or more processors, in response to determining that the signature perturbations are the result of an artifact, overriding an alarm of the patient monitoring device; and with the one or more processors, in response to determining that the signature perturbations are the result of a clinically significant change, invoking the alarm of the patient monitoring device.

15. The method as set forth in claim 14, wherein the wavelet is a Symlet wavelet.

16. The method as set forth in claim 14, wherein each signature is a unique descriptor represented as coefficients that describe a shape variability of a corresponding mapping.

17. The method as set forth in claim 15, further including displaying at least the signatures for observation by clinical staff.

18. A non-transitory computer readable medium having program code embodied therein that when executed by one or more processors, causes the one or more processor to perform a method comprising:
   receiving physiological signals captured by a patient monitoring device indicative of physiological information monitored from a patient;
   with one or more processors, generating a mapping of one physiological signal versus another physiological signal for pairs of the physiological signals as the physiological information for each sampling interval is received;
   with the one or more processors, applying a wavelet decomposition on each mapping to generate a signature for each mapping;
   with the one or more processors, comparing the mapping signatures within and across sampling intervals for signature perturbations;
   with the one or more processors, determining whether the signature perturbations are a result of a clinically significant change or an artifact; and
   with the one or more processors, in response to determining that the signature perturbations are the result of an artifact, overriding an alarm of the patient monitoring device; and
   with the one or more processors, in response to determining that the signature perturbations are the result of a clinically significant change, invoking the alarm of the patient monitoring device.

19. A patient monitoring system, comprising:
   a patient monitoring device;
   a computer programmed to:
   generate morphogram signatures of related patient monitoring signals versus each other from the patient monitoring device;
   decompose the morphogram signatures using wavelet decomposition;
   compare changes in the decomposed morphogram signatures relative to each other or over time; and
   based on the morphogram signature comparisons, determine whether a clinically significant event or an artifact has occurred.

20. The patient monitoring system as set forth in claim 19, wherein the patient monitor includes an alarm and the computer is further programmed to:
   invoke the alarm in response to an event being determined clinically significant; and
   override the alarm in response to determining that an artifact has occurred.

* * * * *